(12) United States Patent
Gerlach et al.

(10) Patent No.: US 6,197,005 B1
(45) Date of Patent: Mar. 6, 2001

(54) CHECK VALVE, IN PARTICULAR FOR USE IN AN IMPLANTABLE ARTIFICIAL BLADDER

(75) Inventors: Roland Gerlach, Guxhagen; Josef Hannappel, Pulheim; Juergen Reuter, Alheim; Dorothea Rohrmann, Langerwehe, all of (DE)

(73) Assignee: CareMed Medical Produkte AG, Dresden (DE)

( * ) Notice: Subject to any disclaimer, the term of this patent is extended or adjusted under 35 U.S.C. 154(b) by 0 days.

(21) Appl. No.: 09/350,284

(22) Filed: Jul. 9, 1999

(30) Foreign Application Priority Data

Jul. 15, 1998 (DE) .............................. 198 31 698

(51) Int. Cl.⁷ ..................................... A61M 5/00
(52) U.S. Cl. ........................... 604/247; 604/246; 137/853
(58) Field of Search ..................... 604/247, 246, 604/537, 30, 288.03, 288.01, 31, 118, 99.02, 99.03, 99.04, 167.01, 167.03, 236, 122, 129, 9, 34, 123, 323; 137/853; 128/DIG. 12

(56) References Cited

U.S. PATENT DOCUMENTS

| 4,084,606 | * | 4/1978 | Mittleman | 137/102 |
|---|---|---|---|---|
| 4,489,750 | * | 12/1984 | Nehring | 137/496 |
| 4,653,539 | * | 3/1987 | Bell | 137/860 |
| 4,811,758 | * | 3/1989 | Piper | 137/844 |
| 5,112,301 | * | 5/1992 | Fenton, Jr. et al. | 604/30 |
| 5,158,539 | * | 10/1992 | Kolff et al. | 604/31 |
| 5,165,493 | * | 11/1992 | Baugh | 175/218 |
| 5,181,921 | * | 1/1993 | Makita et al. | 606/195 |
| 5,401,255 | * | 3/1995 | Sutherland et al. | 604/247 |
| 5,507,436 | * | 4/1996 | Ruttenberg | 239/1 |
| 5,814,004 | * | 9/1998 | Tamari | 604/4 |
| 6,053,896 | * | 4/2000 | Wilson et al. | 604/247 |

* cited by examiner

*Primary Examiner*—Richard K. Seidel
*Assistant Examiner*—Cris Rodriguez
(74) *Attorney, Agent, or Firm*—Diller, Ramik & Wight

(57) ABSTRACT

The check valve comprises an inlet duct (31), an outlet duct (32) and a valve chamber (34) arranged between them. The valve chamber (34) is permanently connected with the inlet duct (31) via openings (35). On a blind duct (33) a valve member (36) is mounted which is made up of a flexible inherently stable hose. The valve member (36) extends into the outlet duct (32) and contacts the inner surface of the outlet duct. At a pressure exceeding the opening pressure of the valve the valve member (36) is lifted off the inner surface of the outlet duct (32).

5 Claims, 3 Drawing Sheets

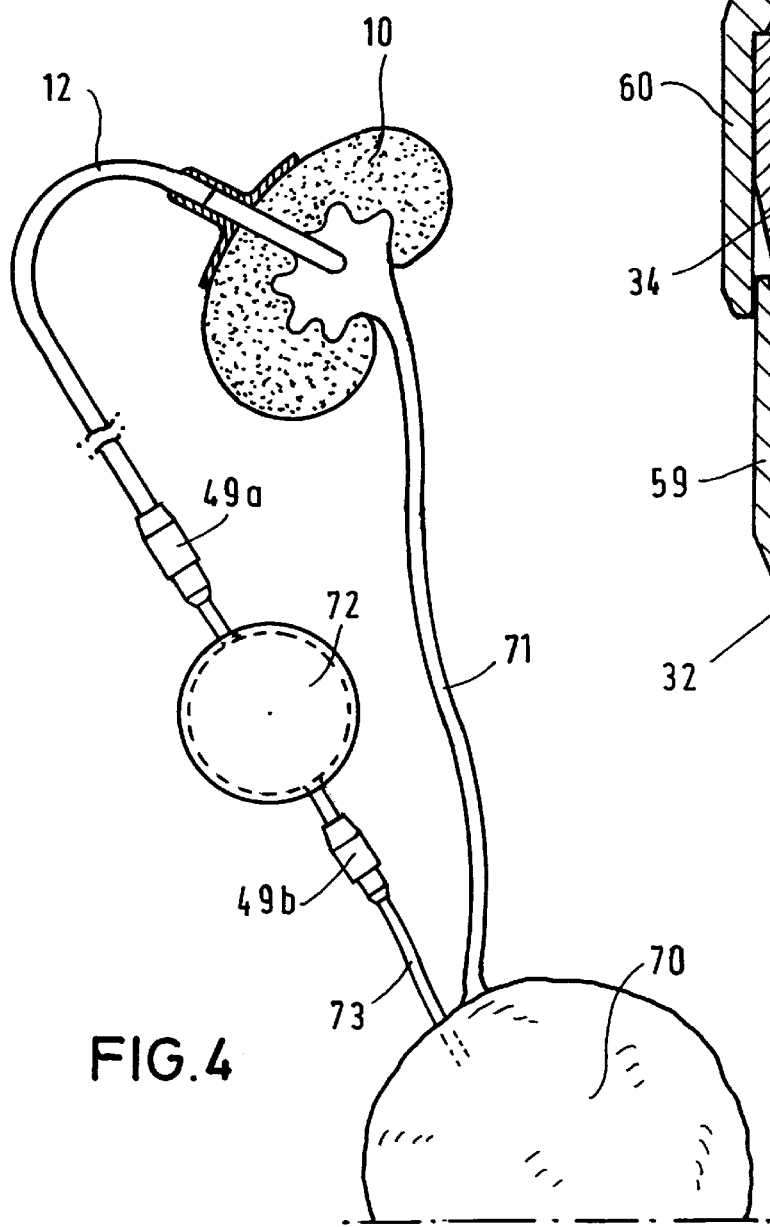
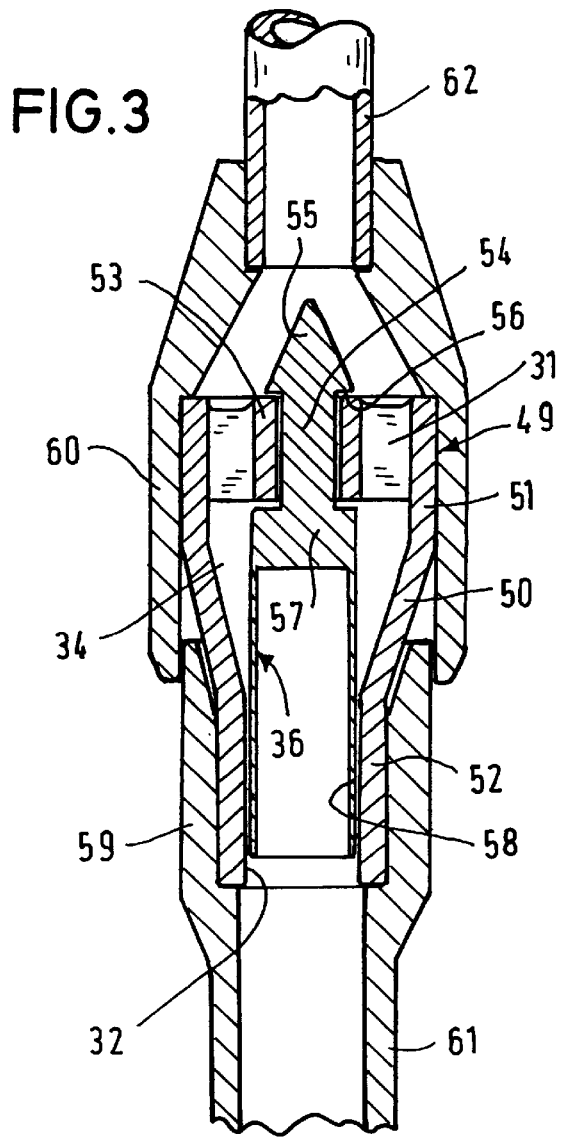
FIG.3
FIG.4

CHECK VALVE, IN PARTICULAR FOR USE IN AN IMPLANTABLE ARTIFICIAL BLADDER

BACKGROUND OF THE INVENTION

The invention relates to a check valve, in particular for use in an implantable artificial bladder, which prevents on the one hand a return flow and has on the other hand a predetermined opening pressure.

There are cases in which check valves are implanted as implants into human bodies. In "The Journal of Urology", Vol. 151, 1996, 2094–2097, an artificial bladder is described which comprises two implant containers which are capable of restoring their original form and which are connected on the one hand through a catheter with the kidneys and on the other hand through a Y-piece with the urethra. The containers, which tend to expand, take up fluid from the kidneys. To discharge the fluid, the patient presses onto the containers so that the fluid flows into the urethra. Each container comprises check valves both at its inlet and its outlet, which prevent on the one hand reflux to the kidney and on the other hand intake of air during the filling phase. These check valves are foil valves which are also referred to as "duckbill valves". Such foil valves have a very low opening pressure so that there is the danger of un-intentional emptying of the containers and thus the danger of incontinence. Furthermore, incrustrations tend to deposit on the implanted foil valves so that these tend to leak.

Artificial bladders with the corresponding valves are also described in EP 0 282 157 B1 and EP 0 393 714 A2. Here relatively complex check valves are provided which involve the danger of failure after they have been implanted for a long time. U.S. Pat. No. 4,497,074 describes a prosthetic bladder. The ureteral catheters leading into the bladder are provided with foil valves.

Furthermore, U.S. Pat. No. 4,722,731 describes a valve comprising a valve member in the form of a flexible hose into which extends an inlet duct from the one end and an outlet duct from the other end. The flexible hose is biased in such a way that it blocks the connection between the inlet duct and the outlet duct. If the opening pressure exceeds a predetermined value, the valve opens. Such a pressure relief valve, too, is of complex design and comprises narrow ducts through which fluid must flow.

SUMMARY OF THE INVENTION

The object of the present invention is to create a check valve of very simple design with a predetermined well-defined opening behaviour.

The check valve according to the present invention is characterized in that the valve member is a flexible and inherently stable hose which is open at one end, and the flowing path runs along its outside. The valve member comprises an open end which extends into the outlet duct. If the pressure in the valve chamber exceeds a limit value, the fluid flows along the outside of the valve member which is thus lifted off the inner surface of the outlet duct. The opening pressure of the check valve can be adjusted by selection of the suitable material or wall thickness of the valve member. It is thus possible to provide a plurality of valve members of different degrees of rigidity and to install one of them into the check valve.

The check valve according to the present invention is particularly suitable for application in connection with artificial bladders. Such bladders require on the inlet side a check valve with a low opening pressure and on the outlet side a check valve with a higher opening pressure. For both check valves the same housing with different valve members can be used.

The check valve is generally suitable as implant or for use in implants. For this purpose it is preferably made of a silicone material. Since silicone materials cannot be welded the valve is assembled of two prefabricated components with the valve member being attached to one of these components by welding, vulcanizing or clamping.

Application of the check valve is not limited to implants or the medical sector. It can be employed in all fields where a predetermined opening behaviour is required, e. g. also in infusion systems.

BRIEF DESCRIPTION OF THE DRAWINGS

Hereunder embodiments of the present invention are explained in detail with reference to the drawings in which FIG. 3 shows another embodiment of the implantable check valve integrated into a line system, and FIG. 4 shows an ureter bypass containing the check valves.

DESCRIPTION OF THE PREFERRED EMBODIMENTS

Figure 1:
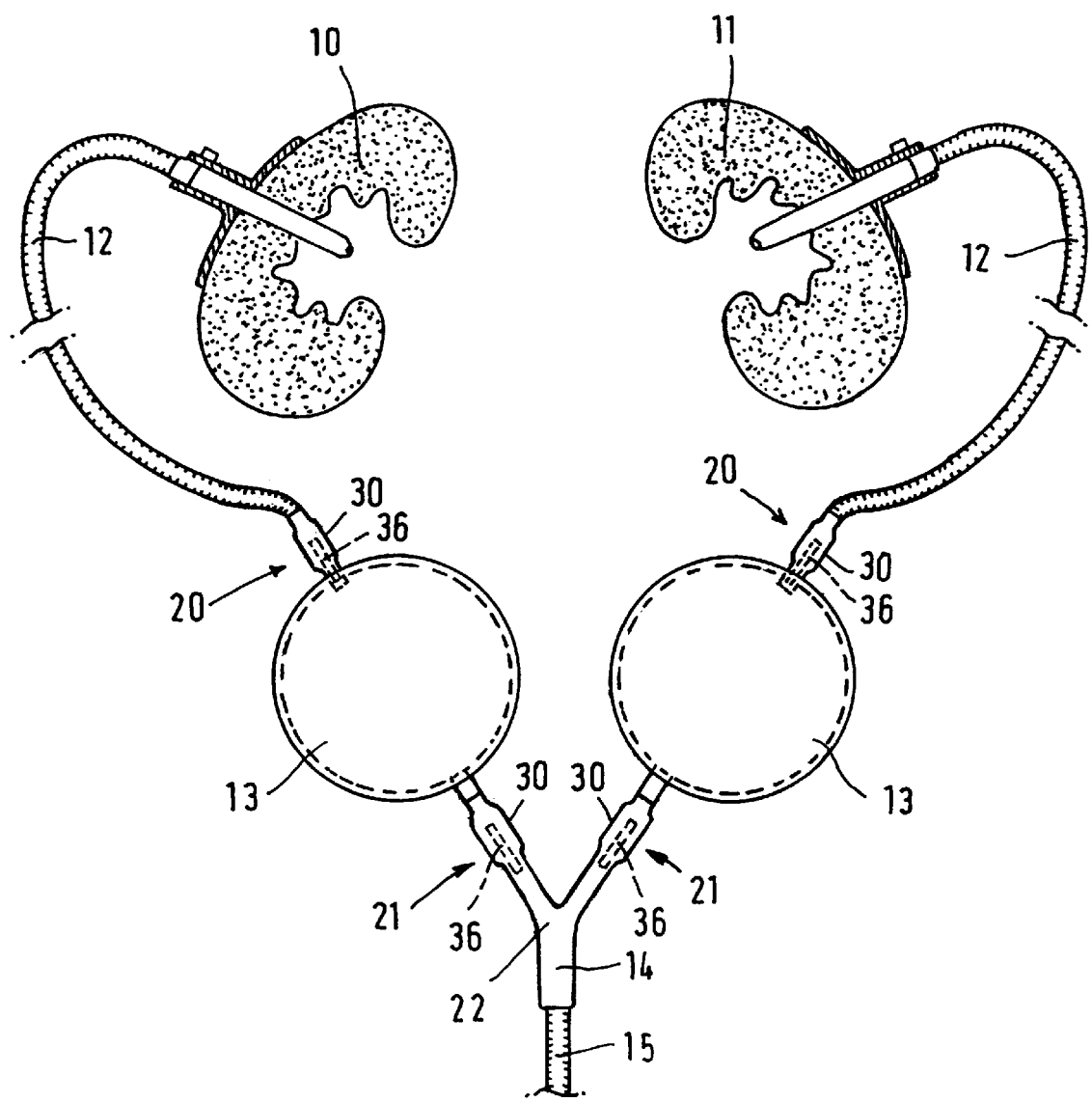
FIG. 1 shows a representation of an artificial bladder in implanted condition.

FIG. 1 shows an artificial bladder system implanted into a patient's body in order to draw urine off the kidneys 10, 11. For this purpose a ureteral catheter 12 is inserted into each kidney with the other end of the catheter being connected to an artificial bladder 13. In the present embodiment two artificial bladders (one for each kidney 10, 11) are provided. Each bladder comprises a flexible container capable of restoring its original form which, in compressed condition, tends to expand thus taking in fluid via the catheter 12. The bladders 13 are implanted subcutaneous in the patient's abdominal region and the patient can press against the bladders from outside with his hand in order to empty the bladders. At the outlet side the bladders 13 are connected to a Y-piece 14 which leads into an artificial or natural urethra 15 with the latter being closed or opened by the sphincter muscle or an external sphincter.

Each bladder 13 comprises a first check valve 20 at its inlet end and a second check valve 21 at its outlet end. The first check valve 20 is open towards the bladder 13 whereas the second check valve 21 is open towards the Y-piece. Both check valves 20, 21 are normally closed and are opened only when a predetermined opening pressure has been reached. In the opposite direction they are permanently closed.

Figure 2:
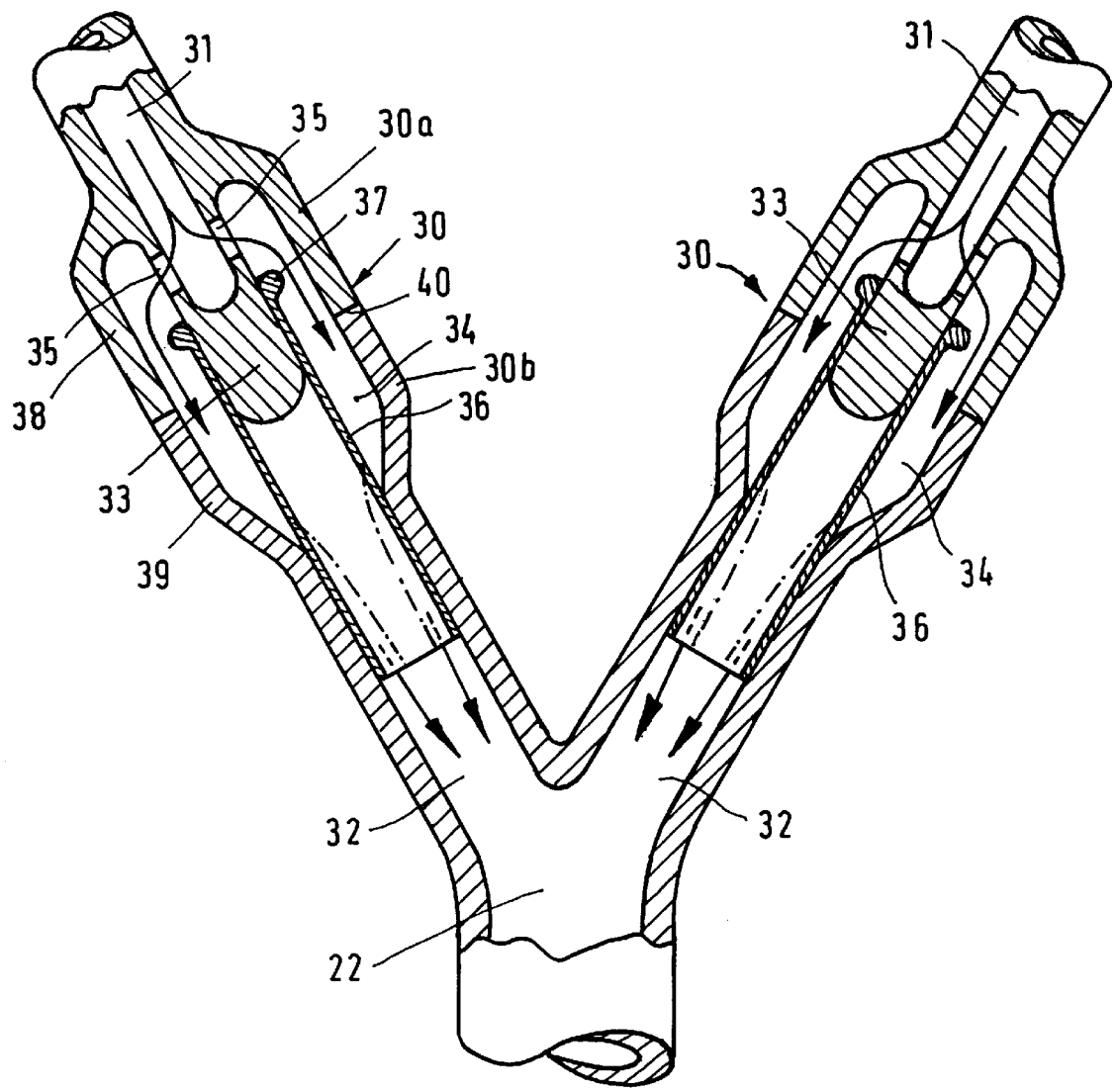
FIG. 2 shows a longitudinal section of two check valves of the bladder system of FIG. 1 with the check valves being combined on the outlet side.

FIG. 2 shows the two check valves 21 connected to the outlets of the bladders 13, whose outlet ducts are combined in the Y-piece 22. The two check valves 21 are of identical design. Each check valve comprises a tubular housing 30 which is connected at one end to the inlet duct 31 and at the other end to the outlet duct 32 to form a single unit. The diameter of the housing 30 is somewhat larger than the outside diameter of the inlet duct 31 and the outlet duct 32. The inlet duct 31 runs into a blind duct 33 arranged coaxially to the inlet duct 31, which extends into a valve chamber 34 inside the housing 30. The blind duct 33 is provided with lateral openings 35 which connect the inlet duct 31 with the valve chamber 34. The inlet duct 31 ends inside the blind duct 33 whose end is closed.

Onto the blind duct 33 a hose-type valve member 36 is drawn which is made up of a flexible and inherently stable hose of plastic foil. This hose is tensionally seated on the blind duct 33. It comprises a torus 37 at its ends, which promotes the hose to be retained on the blind duct. Alternatively or additionally the hose may be glued to the blind duct.

The hose-shaped valve member 36 is hollow and empty (except for the blind duct 33) and extends beyond the valve chamber 34 and into the outlet duct 32. The outside diameter of the cylindrical valve member 36 is dimensioned in such a way that the valve member is slightly pressed against the inner surface of the outlet duct 32 thus isolating the fluid flow from the valve chamber 34. The valve member 36 loosely extends into the outlet duct 32, i. e. it is not permanently fixed to the latter.

The housing 30 is made up of two housing parts 30a, 30b. Each housing part comprises an annular wall 38 and 39 respectively. These annular walls 38, 39 are connected with each other at a connection point 40 and enclose the valve chamber 34. The annular wall 38, the wall of the inlet duct 31 and the blind duct 33 are made of one piece. The annular wall 39 and the wall of the outlet duct 32 are made of one piece.

The housing 30 and the valve member 36 are preferably made of silicone material which is very much tolerated by the body. The housing 30 is substantially rigid while the valve member 36 is a flexible and inherently stable hose. The wall thickness of this hose is selected in dependence on the desired opening pressure. Thus, for example, the check valves 20 at the inlet side of the bladder 13 have an opening pressure of 0.5 cm water gauge whereas the check valves 21 on the outlet side have an opening pressure of 25 cm water gauge. Although the valves 20 and 21 are generally of identical design, they are distinguished from each other by the valve member 36 used.

If the opening pressure in the valve chamber 34 exceeds the respective limit valve, the wall of the valve member 36 is lifted off the inner surface of the outlet duct 32 and the valve becomes permeable. In the opposite direction the valve is always impermeable since a pressure at the outlet duct 32 expands the valve member 36 and presses it even harder against the inner surface of the outlet duct.

The check valve 49 of FIG. 3 comprises a rigid valve housing 50 which is substantially tubular and has an area of a larger diameter 51 and an area of smaller diameter 52 which forms the outlet duct 32. In the area of the larger diameter 51 a ring 53 is located which is retained by a spider. The ring 53 serves as holder for the valve member 36. The valve member 36 is made up of one piece of soft flexible plastic material with different wall thicknesses. It comprises a relatively thick pin part 54 which ends in a tip 55 with an undercut 56 and a holding fixture 57 whose diameter is larger than the inside diameter of the ring 53. The pin part 54, the tip 55 and the holder 57 are massive parts. A cylindrical thin-walled apron 58 extends axially from the holder 57. This apron 58 forms the valve element proper which contacts the inner surface of the outlet duct 32. It forms a soft and easily deformable membrane.

A sleeve 59 partly laps over the valve housing 50 at the outlet side and a sleeve 60 of the outgoing hose line 61 or the incoming hose line 62 partly laps over the valve housing 50 at the inlet side. The sleeve 60 overlaps the sleeve 59 and both sleeves 59, 60 fit closely to the valve housing 50 and enclose the latter. In the overlapping area the sleeves 59, 60 are glued or welded to each other. The hose lines are made of plastic material tolerated by the body, preferably silicone material.

FIG. 4 shows an embodiment where the check valve is used for an ureter bypass. The ureter 71 runs from the kidney 10 to the natural bladder 70. This ureter is peristaltic, i. e. it pumps by muscular movement the urine from the kidney to the bladder. If the ureter is compressed by a tumour or is not capable of functioning properly for other reasons, a ureteral catheter 12 is inserted into the kidney with the catheter 12 being connected subcutaneous to an implanted artificial bladder 72. From the outlet of the artificial bladder 72 a hose 73 runs to the natural bladder 70. At the inlet of the artificial bladder 72 a check valve 49a is located and at the outlet a check valve 49b is located. The artificial bladder 72 is an aspirating bladder capable of restoring its original form which draws urine off the kidney 10. By manual pressure on the artificial bladder 72 the bladder can be emptied via the check valve 49 into the bladder 70. The pumping action manually exerted on the artifical bladder 72 thus substitutes the peristaltic pumping movement of the ureter 71.

When using the ureter bypass system shown in FIG. 4 the surgical intervention into the patient's body is not as heavy as it would be in the case of removal of the natural bladder.

What is claimed is:

1. A check valve particularly adapted for an implantable artificial bladder comprising an inlet duct (31), an outlet duct (32), a valve chamber (34) positioned between the inlet duct (31) and the outlet duct (32), said valve chamber (34) housing a deformable tubular valve member (36), said tubular valve member (36) having a closed end and an open end, the closed end of said valve member (36) being positioned in said valve chamber (34) which is in open fluid communication with said inlet duct (31), an outer surface of the open end of said tubular valve member (36) contacting an inner surface of said outlet duct (32) whereby the tubular valve member (36) can be lifted off the inner surface of the outlet duct (32) when an opening pressure is exceeded, a hollow blind duct (33) extending from the inlet duct (31), said blind duct (33) including at least one opening (35) opening toward the valve chamber (34), and said blind duct (33) closes said closed end of the tubular valve member (36).

2. The check valve as defined in claim 1 wherein said tubular valve member (36) is in external telescopic secured relationship to the blind duct (33).

3. The check valve as defined in claim 1 including a second check valve particularly adapted for an implantable artificial bladder comprising a second inlet duct (31), a second outlet duct (32), a second valve chamber (34) positioned between the second inlet duct (31) and the second outlet duct (32), said second valve chamber (34) including a deformable tubular second valve member (36), said second tubular valve member (36) having a closed end and an open end, the closed end of the second tubular valve member (36) being positioned in the second valve chamber (34) which is in open fluid communication with the second inlet duct (31), an outer surface of the open end of the second valve member (36) contacting an inner surface of the second outlet duct (32) whereby the tubular second valve member (36) can be lifted off the inner surface of the second outer duct (32) when an opening pressure is exceeded, said first and second valve chambers (32, 32) being defined by housings in part defining a Y-structure with the first and second outlet ducts (32, 32) being interconnected.

4. A check valve particularly adapted for an implantable artificial bladder comprising an inlet duct (31), an outlet duct (32), a valve chamber (34) positioned between the inlet duct (31) and the outlet duct (32), said valve chamber (34) housing a deformable tubular valve member (36), said tubular valve member (36) having a closed end and an open end, the closed end of said valve member (36) being positioned in said valve chamber (34) which is in open fluid communication with said inlet duct (31), an outer surface of the open end of said tubular valve member (36) contacting an inner surface of said outlet duct (32) whereby the tubular valve member (36) can be lifted off the inner surface of the outlet duct (32) when an opening pressure is exceeded, said valve chamber (34) being defined by a housing (30) formed of housing parts (30a, 30b), a first housing part (30a) defining said inlet duct (31) opening into a hollow blind duct (33) extending from the inlet duct (31), said blind duct (33) having at least one opening (35) therein, said first housing part (30a) including a first annular wall (38) surrounding the blind duct (33), a second housing part (30b) defining the outlet duct (32), and said second housing part (30b) including a second annular wall (39) connected to said first annular wall (38).

5. A check valve particularly adapted for an implantable artificial bladder comprising an inlet duct (31), an outlet duct (32), a valve chamber (34) positioned between the inlet duct (31) and the outlet duct (32), said valve chamber (34) housing a deformable tubular valve member (36), said tubular valve member (36) having a closed end and an open end, the closed end of said valve member (36) being positioned in said valve chamber (34) which is in open fluid communication with said inlet duct (31), an outer surface of the open end of said tubular valve member (36) contacting an inner surface of said outlet duct (32) whereby the tubular valve member (36) can be lifted off the inner surface of the outlet duct (32) when an opening pressure is exceeded, and said inlet duct (31) includes a coaxial ring (53) surrounding a pin-shaped holding fixture (54) of the tubular valve member (36) housed within a tubular valve housing (50).

* * * * *